United States Patent [19]

Stoudt et al.

[11] 4,430,322
[45] Feb. 7, 1984

[54] MODIFIED GLUCANS AS ANTI-CARIES AGENT AND METHOD OF USE

[75] Inventors: Thomas H. Stoudt, Westfield; Karl H. Nollstadt, Clark, both of N.J.

[73] Assignee: Merck & Co., Inc., Rahway, N.J.

[21] Appl. No.: 372,509

[22] Filed: Apr. 28, 1982

Related U.S. Application Data

[62] Division of Ser. No. 205,030, Nov. 7, 1980, Pat. No. 4,340,675.

[51] Int. Cl.³ .................... A61K 7/16; A61K 31/715; C08B 37/00; C12P 19/18
[52] U.S. Cl. .................................... 424/49; 424/180; 426/658; 435/97; 536/1.1; 536/123; 536/114
[58] Field of Search .................... 536/1.1, 123, 114; 426/658; 424/180, 49; 435/97

[56] References Cited

U.S. PATENT DOCUMENTS

| | | | |
|---|---|---|---|
| 3,705,039 | 12/1972 | Mitsuhashi et al. | 536/1.1 |
| 3,754,925 | 8/1973 | Kimura et al. | 536/1.1 |
| 3,822,250 | 7/1974 | Kimura et al. | 536/1.1 |
| 3,893,996 | 7/1975 | Hamuro et al. | 536/1.1 |
| 4,304,768 | 12/1981 | Staub et al. | 424/180 |

*Primary Examiner*—Johnnie R. Brown
*Attorney, Agent, or Firm*—Gabriel Lopez; Hesna J. Pfeiffer

[57] ABSTRACT

Certain glucans modify the biosynthetic route of extracellular polysaccharides involved in dental plaque development causing critical loss of adhesiveness. They interfere with the biosynthesis of cell-bound polysaccharides reducing and preventing agglutination of cells. They thus aid in the prevention of dental plaque formation or concomitant dental caries and periodontal disease.

9 Claims, No Drawings

MODIFIED GLUCANS AS ANTI-CARIES AGENT AND METHOD OF USE

This is a division of application Ser. No. 205030, filed Nov. 7, 1980 now U.S. Pat. No. 4,340,675.

SUMMARY OF THE INVENTION

This invention relates to improved methods of dental hygiene. More particularly, it relates to a method of preventing dental plaque formation by the oral intake of the glucans of this invention concomitantly with the intake of sucrose or other foodstuff containing sucrose. Even more particularly, it relates to said method where the glucan results from the in vitro (cell-free) glucosyl transferase mediated synthesis of plaque polysaccharides in the presence of enzymes capable of hydrolysis of said plaque polysaccharides. It further relates to commercial sucrose-containing compositions containing an effective amount of said glucans. Still further, it relates to the glucans prepared as described above, and to the process for preparing such glucans.

Extracellular polysaccharides (glucans) elaborated by cariogenic strains of Streptococcus mutans have been identified in human dental plaque and are believed to be involved in the early stages of dental plaque formation which accumulates and ages on the tooth surface, particularly in poorly accessible regions. This plaque permits colonization of cariogenic microorganisms which ultimately produce acid that demineralizes the tooth surface. The presence of certain types of dental plaque is considered a major contributory factor to the subsequent development of a number of pathological conditions such as dental caries and periodontal lesions. Therefore, the prevention of these pathological conditions is a priori, accomplished by the removal of dental plaque or the use of agents that will inhibit or retard the development of it.

It is possible to remove dental plaque mechanically by carefully controlled oral hygiene programs, but the plaque usually re-forms quickly after its removal.

Various dentifrice and mouth wash preparations have been disclosed in the art which purportedly retard plaque formation by incorporating therein antibacterial substances with the intent to interfere with the growth pattern of the oral flora. Ultimately, these agents will interfere with the natural balance of the indigenous oral flora with the result that pathological conditions can develop due to the proliferation of the surviving organisms. Furthermore, they have not achieved any degree of commercial success.

The use of hydrolytic enzymes such as dextranase, [$\alpha$-(1',6) glucan-6-glucanohydrolase] and an [$\alpha$-(1',3)-glucan-3-glucanohydrolase], has been proposed as an effective means of preventing plaque formation, particularly when used in combination. Their use in foods is limited to the extent that these enzymes must be added to prepared or baked foods containing sucrose after the preparation process is completed. The instability to heat of these enzymes does not allow of their addition simultaneously with sucrose to cooking or baking ingredients. Also, shelf-life is limited and therefore, presents a serious problem as a food additive. It is generally proposed that the enzymes be introduced to the oral cavity in a separate act of oral hygiene.

An ideal approach to dental plaque inhibition entails altering the biosynthesis of extracellular and cell-surface plaque polysaccharides in such a manner that plaque is not formed or is formed to a much longer extent. This method should not disturb the natural balance of the oral flora, except for the cariogenic microorganisms which depend on plaque for colonization from saliva.

Surprisingly, the glucans of this invention alter the course of the biosynthesis of extracellular plaque polysaccharides from sucrose so that there results a mixture of extracellular polysaccharides which compositely possess physical properties different from those normally encountered in plaque polysaccharides, such as being much less adhesive. In addition, the glucans of this invention interfere with the biosynthesis of cell-bound polysaccharides from sucrose and prevent cell agglutination which, if not controlled, is the ultimate fate of saliva-suspended cells. Thus, by keeping cariogenic bacteria moving through the oral cavity rather than immobilized on teeth, the progress of cariogenic plaque formation is significantly impaired.

It is an object of this invention to provide a method for the prevention of cariogenic dental plaque formation by the concomitant ingestion of the novel glucans of this invention with sucrose and sucrose-containing foodstuffs.

Another object of this invention is to provide commercial sugar (sucrose) compositions and other commercial sugar-containing compositions containing the novel glucans of this invention thereby reducing the cariogenicity of these abundant food items. The additive retains its activity on exposure to 100° C. for at least 60 minutes, and can, therefore, be a component of all prepared foods containing sucrose, whether canned, baked, or pasteurized.

The objectives are met by addition of the novel glucans of this invention to commercial sucrose and sucrose-containing products, in an amount of 0.1–2% of the sucrose weight, and preferably about 1%.

The glucans of this invention are produced during the cell-free biosynthesis of plaque polysaccharides by glucosyl transferases such as from Streptococcus mutans, Strain SL-1 (NRRL B11025); Streptococcus mutans, Strain GS-5 (NRRL B11026); Streptococcus mutans, Strain LM-7 (NRRL B11027); Streptococcus mutans, Strain NCTC-10449 (NRRL B11031); Streptococcus mutans Strain 06-95 (NRRL B11033); Streptococcus mutans, Strain AHT (NRRL B11032); Streptococcus mutans, Strain E-49, Isolate 6715 (NRRL B11029); Streptococcus mutans, Strain OMZ-176 (NRRL B11030); Streptococcus mutans, Strain K-1R (NRRL B11028); Streptococcus mutans, Strain E-49, (ATCC 31501) and the like, with the important difference that the biosynthetic medium contains from 5–40 units/ml, preferably about 10 units/ml of an $\alpha$-(1$\rightarrow$3)-glucanohydrolase, such as cariogenanase, or a $\alpha$-(1$\rightarrow$6)glucanohydrolase, such as dextranase, capable of hydrolysis of at least some of the $\alpha$(1$\rightarrow$3) or $\alpha$(1$\rightarrow$6) linked polysaccharides of dental plaque. After 24–48 hours of incubation at 37° C., the enzymes of the glucan-generating system are deactivated by autoclaving. The insoluble polysaccharide by-products are separated, for example, by centrifugation or filtration and the glucans of this invention is precipitated from the supernatant by addition of a miscible organic solvent such as an alcohol.

The glucans thus prepared have a molecular weight greater than 500,000 as determined by exclusion on BioGel P-300 and are composed entirely of glucose. They are inert to further attack by an endo-$\alpha$-(1$\rightarrow$3)glucanohydrolase or an endo-$\alpha$-(1$\rightarrow$6)glucan-6- glucanohydrolase. The exact structure in unknown. However, it is presumed that most of the linkages are $\alpha$-(1→3) glucosidic and $\alpha$-(1→6) glucosidic. This deduction is based on the fact that the normal polysaccharides contain polymers with a mixture of these linkages. It is postulated that the polymer is highly branched and there exists an orderly sequence of glucosyl transferases building up the polymer. The presence of either cariogenanase or dextranase in the enzyme system generates an unnatural molecule which will not only go on to be typical sticky plaque material, but in addition, binds the glucosyl transferases in such a way that normal polysaccharide synthesis cannot occur from sucrose. The glucans which inhibit have such a highly specific activity that they are probably suicide enzyme inhibitors for glucosyl transferases of cariogenic microorganisms.

The following examples illustrate the best mode contemplated by applicants for carrying out the instant invention; no limitation, however, being intended except as set forth in the appended claims.

EXAMPLE 1

Preparation of Inhibitory Glucans
Step A: Preparation of cell-free glucosyl transferases Fifteen liters of medium was inoculated with 20 ml of a seed culture of Streptococcus mutans, Strain SL-1, (NRRL-B11025). The medium was of the following composition (per liter):

Trypticase—11 gm.
Yeast extract—5 gm.
Sodium Carbonate—1 gm.
$KH_2PO_4$—13.6 gm.
Glucose—20 gm.
Salt Solution—0.5 ml.

The salt solution had the following composition:
$MgSO_4.7H_2O$—800 mg./100 ml.
$FeCl_3.6H_2O$—48 ml./100 ml.
$MnCl_2$—18 mg./100 ml.

All components with the exception of the glucose were dissolved in 14,500 ml. of distilled water, the pH adjusted to 7.2 with 2 N NaOH, and autoclaved for 40 minutes. The glucose was separately autoclaved in 5×100 ml. batches for 15 minutes. Good growth developed within a few hours, and the culture was harvested after 16 hours, when the pH had dropped to 6.2. To arrest the growth the culture was chilled by placing it in an ice-bath and the cells were separated by centrifugation through a centrifuge with a relative centrifugal force (RCF) of approximately 26,400×g. The clear effluent at 4° C. was then treated immediately with dry ammonium sulfate (500 gm./liter). The resulting suspension was stored at 4° C. for 24 hours. The salted-out materials, including the desired glucosyl transferases, were collected by centrifugation at 26,400×g as a gummy paste. The effluent was discarded.

Step B: Preparation of Inhibitory Glucans
1. Use of Cariogenanase

The paste from Step A was dissolved in 400 ml of ice-cold, 0.05 M phosphate buffer at pH 6.5 to give a slightly turbid solution. This solution was added to 2 liters of a 6% sucrose solution in 0.05 M phosphate buffer, pH 6.5 and also containing 1.0 gm of cariogenanase, (35 units/ml.). To assure sterility the incubation system was charged with sodium azide to 0.02% (W/V). The incubation was carried out under stationary conditions at 37° C. for 48 hours. The system was then deactivated in a steam autoclave for 30 minutes, with temperature control to 100° C. The deactivated system was allowed to stand in the cold for 24 hours. The system was then cleared by centrifugation at 23,000×g for 60 minutes at 4° C. in 250 ml centrifuge cups. The slightly opaque supernatant was siphoned off and was then diluted slowly with one volume of 95% ethanol. The resulting suspension was allowed to stand at ambient temperature for 24 hours to allow clearing by sedimentation. A firm layer of a gel sedimented allowing the total removal of the supernatant by siphoning. The gel was redissolved in 800 ml of 0.5 M sodium acetate buffer pH 7.0. The glucans were re-precipitated by the addition of 1 volume of 95% ethanol. After it had sedimented and the supernatant was removed, the gel was washed twice in 500 ml of 50% ethanol. The product was dissolved in 500 ml distilled water to give a viscous and slightly turbid solution. It was stored frozen for further use. It assayed for 15.4 mg. glucose/ml by the phenol-sulfuric acid method. The solution of the product could also be freeze-dried, but was found difficult to re-hydrate and solubilize. It is, however, easily re-hydrated when freeze-dried from a solution of the following composition: 15.4 ml. glucan+100 mg mannitol per milliliter.

2. Use of Dextranase

Employing the method described in Step B, Part 1, but substituting for cariogenanase, dextranase at 10 units/ml, a modifying glucan may be obtained having a different structure and characteristics since for its obtainment from 55-70% ethanol are required for its insolubilization.

Employing the technique of Step A, glucosyl transferases may be prepared by substituting for the *Streptococcus mutans*, Strain SL-1, (NRRL-B11025) or other Streptococcus species such as those noted above. The glucosyl transferases so produced then may be employed in the preparation of the inhibitory glucan using the technique described in Step B.

EXAMPLE 2

Demonstration of Inhibitory Action of Dextrananase-Produced Inhibitory Glucan
1. Preparation of Inhibitory Glucans The inhibitory glucans were prepared in a cell-free culture broth of *Streptococcus mutans*, Strain SL-1 (NRRL-B11025). The growth medium was compositioned by dialysing a solution of 11 gm of trypticase and 5 gm of yeast extract in 100 ml of distilled water against 900 ml of distilled water in a hollow fiber dialyser by use of a pressure gradient. To the dialysate was added potassium phosphate (to 0.1 M, pH 7.0 with 1 N sodium hydroxide), 900 mg sodium carbonate, 18 gm dextrose (to 2%), and 0.25 ml of a solution of trace elements ($MgSO_4.7H_2O$ 200 ml; $FeCl_316H_2O$ 40 ml; $MnCl_2$ 18 mg dissolved in 100 ml water) The medium was filtered into sterile disposable filter units, 0.45 micron pore size, 100 ml capacity. The filtrate was inoculated with 1.0 ml of a seed culture of *Streptococcus mutans*, Strain SL-1. The cultures were harvested, usually after 6 to 8 hours, when the pH had reached a level of about 6. The cells were removed by centrifugation at 15,000 rpm for 20 minutes at 2° C. in 50 ml cups. Sixty-five milliliters of the supernatant was added to 10.0 cc of 0.2 M phosphate buffer at pH 6.5, containing 3.75 gm of sucrose such that the final sucrose concentration in the system was 5%. The system was also charged with dextranase from *Penicillium funiculosum*, prepared by the method of Chaiet et al. (Applied Microbiology, Vol. 20, pg.

420-421, 1970) to an activity level of 10 units/ml. The system was then filtered into sterile filter units and incubated for 24 hours at 37° C. The insoluble polysaccharides formed during the incubation period were removed by centrifugation at 15,000 rpm, for 20 minutes at 2° C., in 50 ml cups and the clear supernatant was steam-autoclaved (100° C.) for 60 minutes to deactivate any extraneous enzymatic activity including the dextranase.

2. Preparation of Control System

Sixty-five milliliters of cell-free culture broth and 10.0 ml of 0.2 M phosphate buffer at pH 6.5 containing 3.75 gm sucrose were separately steam-autoclaved (100° C.) for 60 minutes, cooled and combined and used as such as controls.

3. Insoluble Polysaccharide Synthesizing Systems

The polysaccharide synthesizing system consisted of cell-free broth of *Streptococcus mutans*, Strain SL-1, prepared as per 1 above. For the systems containing the modifier oligosaccharides, 40 ml of the cell-free broth was added to 10.0 ml of the modifier solution in which were dissolved additional 2.0 gm of sucrose before mixing such that the final concentration of sucrose was 5% in a system of 50 ml. After mixing, the solution was filtered into sterile filters, 0.45 micron pore size, and incubated at 37° C. for 48 hours. The controls were similarly prepared with the control solution. Duplicate or triplicate systems were used as a matter of routine. At the end of the incubation cycle the insoluble polysaccharides were suspended with 10 brisk swirls by hand and decanted. The physical properties of adhesiveness of the polysaccharides was judged by the absence or presence of an opaque film on the bottom of the filter unit after decantation and air-drying of the adhering polysaccharides. Typically, the control deposits are opaque to printed matter, placed beneath the filter unit, while the modifier-containing systems are devoid of any deposits whatsoever.

4. Analysis of Insoluble Polysaccharides

For chemical analysis the insoluble polysaccharides were transferred quantitatively into appropriate centrifuge cups and washed sequentially with water (3 times), ethanol (twice) and acetone; they were then dried in vacuo over $P_2O_5$ for 24 hours. The following analytical parameters were judged essential for a meaningful interpretation: (1) Total insoluble polysaccharides synthesized (as glucose) per system of 50 ml; (2) Total insoluble dextranase-resistant polysaccharide formed per system (as glucose). (3) Total insoluble dextranase-sensitive polysaccharide formed per system (as glucose) and (4) Periodate-sensitivity of dextranase-resistant polysaccharide in both control and modified system. Dextran levels of biosynthesized insoluble polysaccharides were estimated by the anthrone method (Anal. Chem., Vol. 25, Page 1656, 1953) after maximal hydrolysis had been achieved with purified dextranase from *Penicillium funiculosum* (Chaiet et al. supra). Total polysaccharide in a dry sample of the isolates was estimated by the anthrone method and the level of dextranase-resistent polysaccharide (cariogenan) was established by difference. Periodate oxidation was carried out on the dextranase-refractory polysaccharide, cariogenan, after maximal hydrolysis has been achieved with dextranase. The refractory material was washed and dried as described above. The dried material was suspended (3.00 mg/ml) in 0.012 M sodium metaperiodate and kept at 4° C. for 170 hours, totally shielded against light. The reaction vessels were kept on a rotating incubator during that time. It could be established that maximal periodate uptake took place during this time interval. The excess periodate was determined by microtitration with standard sodium-arsenite solution (0.01201 M). All analytical results are compiled in the following table.

BIOSYNTHESIS OF INSOLUBLE STREPTOCOCCAL POLYSACCHARIDES IN A CELL-FREE SYSTEM OF *STREPTOCOCCUS MUTANS*, STRAIN DL-1 IN THE ABSENCE AND PRESENCE OF MODIFIER OLIGOSACCHARIDES

| System | Optical Density (620 mμ) Anthrone Test* | Dextran** μgm/mg dry weight | Dextranase-Refractory Polysacch. μgm/mg dry weight | Dextran Biosynthesized per ml System μgm | Dextranase-Refractory Polysacch. Biosynthesized per ml System μgm | Ratio Refractory Dextran | % Periodate Sensitivity of Refractory Polysacch.*** |
|---|---|---|---|---|---|---|---|
| Control #1 | .40 | | | | | | |
| | .41 | Avg. 334 | 666 | 250 | 500 | 2.00 | 26.4 |
| Control #2 | .42 | | | | | | |
| Modifier #1 | .530 | | | | | | |
| | .535 | Avg. 437 | 563 | 312 | 400 | 1.28 | 29.5 |
| Modifier #2 | .540 | | | | | | |

*Optical Density (at 620 mμ) by Anthrone method, 1.0 mg sample/ml
**Corrected for water gain on hydrolysis
***Average of 2 Determinations No significant differences in the periodate uptake were noted and it may be possible that the structural characteristics of the dextranase-refractory polysaccharides in either system remained unchanged.

5. Effect of Streptococcal Modified (Oligosaccharide) on the Polysaccharides of a Mixed Culture of the Human Mouth.

The effect was studied in a cell-free synthesizing system. The polysaccharide synthesizing system consisted of a cell-free broth prepared as per 1., above, except that the inoculum was a culture obtained by suspensions of dental plaque scrapings taken from a human mouth. A seed culture was prepared in 10 ml medium. The mixed culture developed, as well as, the pure culture of *Streptococcus mutans*, Strain SL-1, and was harvested after 6 hours when the pH had dropped to about 6. The composition of the control and modifier-containing systems were identical to those described in 3., above, for the pure culture studies. The effect of the modifying oligosaccharides on the biosynthesis of insoluble polysaccharides by the sucrose-transferases of a mixed culture was very much the same as that observed in a pure streptococcal system.

EXAMPLE 3

Demonstration of Inhibitory Action of The Glucan Obtained With the Addition of Cariogenanase The effect of the inhibitory glucan has been demonstrated in three ways:
  (A) The modification of in vitro dental plaque produced in a cell-free system, the product being much less adhesive;
  (B) The interference with normal cell-surfact synthesized polysaccharide in such a way that cell agglutination and immobilization does not occur or is otherwise impaired; and
  (C) As a result of the modifying effects demonstrated in (A) and (B) above, a marked remission of plaque-on-wire formation ascribable to the addition of the modifying glucan.

Experimental Protocols

A. The modification of in vitro dental plaque produced in a cell-free system; the product being much less adhesive.

| Additions | Control System | Modified System |
|---|---|---|
| SL-1 Cell-Free+ broth, pH 6.2 | 30.0 ml | 30.0 ml |
| Modifier++ Generator Supernatant | — | 10.0 ml |
| 0.1 M Phosphate Buffer, pH 6.5 | 10.0 ml | — |
| Sucrose, 40% in 0.1 M Phosphate Buffer pH 6.5 + Thimerosal 1:5,000 | 10.0 ml | 10.0 ml |

Incubation in Nalgene Plastic Filter units, 100 cc cap. (in triplicate) at 37° C., stationary, for 24 hours.
+Medium composition described under Example 1
++SL-1 cell-free broth, (60 ml) + 20 ml 24% sucrose in 0.1 M phosphate beffer, pH 6.5 + 2,000 units cariogenanase, incubation for 24 hours at 37° C.; deactivated by heating at 100° C. for 30 minutes; clear supernatant obtained by centrifugation.

The difference in adhesive properties of the resulting polysaccharides was demonstrated by agitation of the cups and decantation of the suspended polysaccharides. As a result, the modifier-containing cups were left practically free of residual and adhering polysaccharide, while the controls retained a heavy residue of adhering polysaccharide.

B. The interference with normal cell-surface synthesized polysaccharide in such a way that cell agglutination and immobilization does not occur or is otherwise impaired.

| Additions | 1 Dextrose Control | 2 Modifier No Sucrose | 3 | 4 | 5 | 6 | 7 |
|---|---|---|---|---|---|---|---|
| Cell Suspension + 9249-165 | 2 ml. | 2 ml. | 2 ml. | 2 ml. | 2 ml. | 2 ml. | 2 ml. |
| Sucrose in 0.1 M PO$_4$ Buff pH 6.5 10% | — | — | 2 ml. | 2 ml. | 2 ml. | 2 ml. | 2 ml. |
| Dextrose in 0.1 M PO$_4$ Buff pH 6.5 10% | 2 ml. | 2 ml. | — | — | — | — | — |
| Modifier 15.4 mg./ml. | — | 100 μl | 100 μl | 50 μl | 25 μl | 10 μl | 0 — |
| Degree of Agglutination++ | 0% | 0% | 0% | 0% | 0% | 10% | 44% |

+Washed cells Streptococcus mutans, strain E-49, NRRL-B11029, in buffered saline (Dulbecco); O.D.$_{620.670}$
++O.D.$_{620}$ taken at zero time and 5 hrs. incubation at 37° C. after filtration through S & S filter disc 740-E, ⅛" mounted in Millipore's Sweeny Adaptors by gravity. Percent agglutination estimated from otical density differentials.

C. As a result of the modifying effects demonstrated in A. and B. above, a marked remission of plaque-on-wire formation ascribable to the addition of the modifying glucan.

Streptococcus mutans, Strain SL-1, (NRRL-B11025), was grown in 12 ml of the medium described in Example 1, except that the dextrose was substituted with sucrose (60 g./liter) in a 25 ml test tube into which was introduced a nichrome wire, suspended from a stopper. The set-up was prepared in triplicate, and the modifying glucan was added to the proper tubes at a level of 0.5% with respect to sucrose. In the first incubation bycle the systems were incubated for 24 hours at 37° C. For the second incubation cycle of 24 hours all nichrome wires were transferred under sterile conditions into tubes containing fresh medium. The manipulation was repeated once more for a third 24 hours cycle of incubation. The wires were then transferred into buffered isotonic saline solution and the developed plaque was observed. The plaque-on-wire was profiled by photography and the respective volumes of the cylindrical deposits were estimated from the diameters of the deposit and the wire. Thus, a 4:1 volume ratio was found in favor of the control plaques.

EXAMPLE 4

Attempt to Prepare Inhibitory Glucans by Controlled Acid Hydrolysis of Cariogenan The possible modifying effect of solubilized cariogenan was studied as it may relate to the biosynthesis of insoluble polysaccharides produced by Streptococcus mutans. The hydrolysates were prepared in the following manner: 300 mg of cariogenan (SL-1 strain), was suspended in 3.0 ml of 66% sulfuric acid and the resulting suspension were kept at room temperature for 15 and 60 minutes, respectively. The hydrolysates were then diluted with distilled water to 84 ml and the suspensions ere neutralized by addition of a saturated solution of barium hydroxide. The barium sulfate was removed by centrifugation and the clear supernatants were aerated with CO$_2$ until the pH remained constant at 6. Again the suspensions were centrifuged to remove barium carbonate. The clear supernatants were aerated with filtered air to remove the excess carbon dioxide. The volume was adjusted to 200 ml and the hydrolysates used as an additive in plaque-on-wire experiments described in detain in Example 3, part C. The hydrolysates were added (1.0 ml each, or approximately 1.5 mg cariogenan equivalent) to ml plaque-on-wire system.

The plaque deposits which developed under these conditions were found normal with respect to the control plaques and no modifying effect could be ascribed to the addition of the hydrolysis products of cariogenan. The 15 minute hydrolysate of cariogenan was particularly viscous indicating the presence of soluble but high molecular weight glucans as hydrolysis products.

EXAMPLE 5

Attempt to Prepare the Inhibitory Glucan by Enzymatic Hydrolysis of Cariogenan

The possible modifying effect of solubilized cariogenan was studied as it may relate to the biosynthesis of insoluble polysaccharides produced by *Streptococcus mutans*. The hydrolysate was prepared in the following manner: 15 mg of cariogenan (SL-1 Strain), was suspended in 1.0 ml of 0.1 M phosphate buffer, pH 6.5 and charged with 5 ml of cariogenanase (500 units per mg) and 0.5 mg sodium azide (0.02%. The suspension was incubated for 18 hours at 37° C. then placed in a boiling water bath for 30 minutes to deactivate the enzyme. The digest was filtered. The clear filtrate assayed for 4.7 mg/ml total hexose, as dextrose, by the phenol-sulfuric acid method. The experimental protocol and the results given below. The optical densities of the systems were measured after filtering the incubation mixtures by gravity after 5 hours incubation at 37° C. It can be seen that enzymatic hydrolysis products of cariogenan have no effect on the rate or extent of cell agglutination.

The Effect of Cariogenanase-on-Cariogenan Hydrolysis Products on the Rate of Cell-Agglutination

| Additions | Tube No. (In Duplicates) | | | | | |
|---|---|---|---|---|---|---|
| | 1 | 2 | 3 | 4 | 5 | 6 |
| Cell-Suspension NRRL-B11029 O.D.$_{620}$ 0.65, in buffered saline | 2.00 ml. | 2.00 | 2.00 | 2.00 | 2.00 | 2.00 |
| Cariogenanase-on-Cariogenan Hydrolysis Prod. 4.7 mg. dextrose/ml. | — | — | 0.20 | 0.20 | — | — |
| 10% sucrose in 0.1 M phosphate buffer, pH 6.5 | — | — | 2.00 | 2.00 | 2.00 | 2.00 |
| Buffer, 0.1 M phosphate pH 6.5 | 2.00 | 2.00 | — | — | 0.20 | 0.20 |
| Time at which Cell Agglutination Occurred | | | 60 Min. | 60 Min. | 80 Min. | 80 Min. |
| Degree of Cell Agglutination 5 hours of incubation | | | 63% | 39% | 49% | 45% |

EXAMPLE 6

Preparation of Cariogenan by Streptococcus mutans in vitro

The starting material in the isolation of cariogenan was produced in a medium of the following composition: 5 gm yeast extract, 11 gm trypticase, 60 gm sucrose, 1 gm $Na_2CO_3$, 0.5 ml salt solution ($mgSO_4.7H_2O$; 800 mg; $FeCl_3.6H_2O$; 40 mg; $MnCl_2$: 18 mg per 100 ml deionized water) dissolved in 1 liter of 0.1 M phosphate buffer, pH 7.3. The medium was inoculated with *Streptococcus mutans*, Strain SL-1 (NRRL-B11025) and the insoluble material was harvested when the pH had dropped to about 5.2. Following centrifugation, the material was washed twice with 20 volumes of deionized water and freeze-dried.

The polysaccharides (10 gm) were extracted at room temperature with 1 liter of 0.5 M NaOH with constant stirring for 30 minutes. The insolubles were removed by centrifugation and discarded. The slightly opaque supernatant was brought to pH 5.1 by adding 2 N acetic acid, with formation of a heavy gel. The volume of the very viscous suspension was noted and 200 units/ml of dextrananase was added. The suspension was incubated at 37° C. until the anthrone-positive sugars, solubilized by the dextrananase, had reached a maximum level. This usually required from 6 to 8 hours. The dextrananse digest which had become less viscous, was centrifuged to collect the undigested materials. The pelleted materials were washed twice in 10 volumes of 0.5 N NaOH and deproteinized with an equal volume of chloroform:butanol (9:1 v/v) in a blender at low speed for 15 minutes. The chloroform-protein complex was removed by separation of the phases in the centrifuge. The clear aqueous layer was recovered by siphoning, and the deproteinization step repeted until the chloroform-protein complex appeared as a thin skin partially covering the interphase. The clear and almost colorless aqueous phase was dialyzed overnight against running deionized water. On loss of alkalinity, cariogenan settled out as a white, translucent gel, consisting of flat, shiny particles.

EXAMPLE 7

Production of Cariogenanase with Cariogenan as Carbohydrates Source

Production of cariogenanase was carried out in 2 liter unbaffled flasks containing 400 ml of medium of the following composition: 800 mg of nutrient broth, 800 ml of yeast extract, 800 ml of trypticase, 0.20 ml of salt solution (same as above), 8 gm of cariogenan (not essential for all cultures); in 400 ml of 0.1 M phosphate buffer, pH 7.0. After autoclaving (15 minutes at 121° C.), the medium was inoculated with 1 ml of a 48 hour seed culture brought up in 50 ml (250 ml shake-flask) of a dextrose medium, composed as follows: Aradamine (autolyzed yeast from Yeast Products, Inc.), 10 gm; dextrose, 10 gm; $KH_2OP_4$,180 mg; $Na_2HPO_4$, 190 mg; $MgSO_417HO_4$, 50 mg; dissolved in 1 liter of distilled water. The production culture was incubated at 37° C. on a shaker at 200 rpm with 2" throw. The culture was harvested when the suspended cariogenan had cleared, usually between 72 and 96 hours.

The broth was cleared of cells and other residual insolubles by centrifugation at 2° C. for 20 minutes, 16,000×g. Ghe clear supernatant was concentrated *in vacuo* (400 ml to 40 ml), and acetone at −60° C. was added to the concentrate in an ice-bath with stirring in 2-3 ml portions to a final concentration of 60% (vol/-vol). The precipitated materials were collected by centrifugation, 1500×g for 10 minutes at −20° C. The precipitate was immediately suspended in 200 ml of ice-cold 0.05 M phosphate buffer, pH 7.0. The resulting suspension was stirred for 60 minutes and then cleared of insolubles by centrifugation at 13,000×g for 20 minutes at 2° C. The clear, pale yellow supernatant was then brought to saturation with respect to $(NH_4)_2SO_4$. The precipitate was collected by centrifugation at 13,000×g for 20 minutes at 2° C. The precipitate was dissolved in 40-60 ml of ice-cold distilled water and dialyzed for 24 hours. The clear solution was freeze-dried. The resulting material (yield: 150–200 mg) assayed for 400–550 units/ml cariogenanase activity.

As pointed out above, the modified glucans of this invention find their most useful application as additives to commercial sucrose and sucrose-containing foodstuffs. Although the modifying effect of the glucans of this invention is essentially independent of the absolute concentration of sucrose, being more closely related to the concentration of free or cell-bound glucosyl transferases (e.g. density of viable cell in the streptoccal system), it is convenient for purposes of application to employ the modified glucan in quantities based on sucrose content. As additives to commercial sucrose and sucrose-containing foodstuffs, the modified glucans of this invention are employed in quantities ranging from about 0.1 to 3% by weight based on total sucrose concentration. The preferred concentration is about 1% mofified glucan by weight based on total sucrose content. The following formulations illustrate preferred embodiments:

1. A 1% solution of the modifying glucan in molasses or syrups (based on the total sucrose concentration in the syrup).
2. One percent modifying glucan powdered sugar, with the addition of the modifier, either alone or in a suitable dry ingestible carrier, such as mannitol in a weight ratio of 4–8 (carrier), 1 (glucan).
3. Addition of the modifying glucan to sucrose refining liquors at such percentage levels that the glucan appears as a contaminant in crystalline, refined sugar at formulation specifications of 1%.

In addition, it will be obvious to those skilled in the art that the mofified glucans of this invention can be employed in the 0.1–3% by weight range as additives to oral hygene preparations such as dentifrices, toothpowders, mouth washes and prophylaxis pastes as used in professional dental hygene.

The subject matter which applicants regard as their invention is particularly pointed out and distinctly claimed as follows:

1. A glucan with a molecular weight in excess of 500,000, consisting predominantly of $\alpha$-(1→3)glucosidic bonds and inert to enzymatic attack by an endo-$\alpha$-(1→3)-glucan-3-glucanohydrolase produced by the process which comprises cell-free biosynthesis of plaque polysaccharides in a biosynthetic medium containing from 5–40 units/ml of the endo-$\alpha$-(1→3)glucan-3-glucanohydrolase for 24–48 hours at 37° C., inactivating the enzymes, removing insoluble polysaccharides and adding a miscible organic solvent to precipitate the desired glucan.

2. A glucan produced by the process of claim 1 wherein the endo-$\alpha$-(1→3)glucan-3-glucanohydrolase is cariogenanase.

3. A foodstuff composition comprising sucrose and an effective amount of the glucan of claim 1.

4. A foodstuff composition comprising sucrose and an effective amount of the glucan of claim 2.

5. A glucan with a molecular weight in excess of 500,000, consisting predominantly of $\alpha$-(1→6)glucosidic bonds, and inert to enzymatic attack by an endo-$\alpha$-(1→6)-glucan-6-glucanohydrolase produced by the process which comprises cell-free biosynthesis of plaque polysaccharides in a biosynthetic medium containing from 5–40 units/ml of the endo-$\alpha$-(1→6)glucan-6-glycanohydrolase for 24–48 hours at 37° C., inactivating the enzymes, removing insoluble polysaccharides and adding a miscible organic solvent to precipitate the desired glucan.

6. A glucan produced by the process of claim 5 wherein the endo-$\alpha$-(1→6)glucan-6-glucanohydrolase is dextranase.

7. A foodstuff composition comprising sucrose and an effective amount of the glucan of claim 5.

8. A foodstuff composition comprising sucrose and an effective amount of the glucan of claim 6.

9. A method of inhibiting dental plaque, caries and periodontal disease which comprises ingesting an effective amount of the glucan of claim 6 concomitantly with a sucrose-containing foodstuff.

* * * * *